US00PP22351P2

(12) United States Plant Patent
Kako et al.

(10) Patent No.: US PP22,351 P2
(45) Date of Patent: Dec. 13, 2011

(54) ***TORENIA* PLANT NAMED 'SUNREKODOU'**

(50) Latin Name: ***Torenia* sp.**
Varietal Denomination: Sunrekodou

(75) Inventors: Tetsuya Kako, Shiga (JP); Kenichi Suzuki, Osaka (JP); Takeshi Kanaya, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/927,780

(22) Filed: Nov. 22, 2010

(51) Int. Cl.
*A01H 5/00* (2006.01)

(52) U.S. Cl. ..... Plt./487

(58) Field of Classification Search ..... Plt./487
See application file for complete search history.

*Primary Examiner* — Kent L Bell
(74) *Attorney, Agent, or Firm* — C. A. Whealy

(57) ABSTRACT

A new and distinct cultivar of *Torenia* plant named 'Sunrekodou', characterized by its compact and mounding to trailing plant habit; freely branching habit; freely flowering habit; yellow and violet-colored flowers; and good garden performance.

1 Drawing Sheet

Botanical designation: *Torenia* sp.
Cultivar denomination: 'SUNREKODOU'.

BACKGROUND OF THE INVENTION

The present invention relates to a new and distinct cultivar of *Torenia* plant, botanically known as *Torenia* sp. and hereinafter referred to by the name 'Sunrekodou'.

The new *Torenia* plant is an induced mutation of a proprietary selection of *Torenia* sp. identified as code number 06-13-7, not patented. The new *Torenia* plant was discovered and selected by the Inventors as a single plant from within a population of plants of induced mutations of the parent selection in a controlled greenhouse environment in Higashiomi, Shiga, Japan in January, 2008.

Asexual reproduction of the new *Torenia* plant by vegetative cuttings in a controlled greenhouse environment in Higashiomi, Shiga, Japan since February, 2008, has shown that the unique features of this new *Torenia* plant are stable and reproduced true to type in successive generations.

SUMMARY OF THE INVENTION

Plants of the new *Torenia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunrekodou'. These characteristics in combination distinguish 'Sunrekodou' as a new and distinct cultivar of *Torenia:*

1. Compact and mounding to trailing plant habit.
2. Freely branching habit.
3. Freely flowering habit.
4. Yellow and violet-colored flowers.
5. Good garden performance.

Plants of the new *Torenia* differ primarily from plants of the parent selection in flower color as plants of the parent selection have yellow and brown-colored flowers.

Plants of the new *Torenia* can be compared to plants of *Torenia* 'Danmoon20', disclosed in U.S. Plant Pat. No. 19,176. In side-by-side comparisons conducted in Higashiomi, Shiga, Japan, plants of the new *Torenia* and 'Danmoon20' differed in the following characteristics:

1. Plants of the new *Torenia* were more compact than plants of 'Danmoon20'.
2. Plants of the new *Torenia* had shorter internodes than plants of 'Danmoon20'.
3. Plants of the new *Torenia* had larger flowers than plants of 'Danmoon20'.
4. Plants of the new *Torenia* and 'Danmoon20' differed in flower color.

BRIEF DESCRIPTION OF THE PHOTOGRAPHS

The accompanying colored photographs illustrate the overall appearance of the new *Torenia* plant showing the colors as true as it is reasonably possible to obtain in colored reproductions of this type. Colors in the photographs may differ slightly from the color values cited in the detailed botanical description which accurately describe the colors of the new *Torenia* plant.

The photograph at the top of the sheet comprises a side perspective view of a typical flowering plant of 'Sunrekodou' grown in a container.

The photograph at the bottom of the sheet is a close-up view of a typical flowering plant of 'Sunrekodou'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical for commercial *Torenia* production. During the production of the *Torenia* plants, day temperatures averaged 23° C. and night temperatures averaged 15° C. Plants were six months old when the photographs and description were taken. In the following description, color references are made to The Royal Horticultural Society Colour Chart, 2007 Edition, except where general terms of ordinary dictionary significance are used.

Botanical classification: *Torenia* sp. 'Sunrekodou'.

Parentage: Induced mutation of a proprietary selection of *Torenia* sp. identified as code number 06-13-7, not patented.

Propagation:

*Type.*—By vegetative cuttings.

*Time to initiate roots.*—About one week at 20° C. to 25° C.

*Time to produce a rooted young plant roots.*—About three to four weeks at 15° C. to 20° C.

*Root description.*—Fibrous; white in color.

*Rooting habit.*—Freely branching.

Plant description:

*Plant form/habit.*—Compact and mounded to trailing plant habit; outwardly spreading; vigorous growth habit; freely branching habit with numerous lateral branches developing per plant, pinching enhances branching potential.

*Plant height.*—About 16 cm.

*Plant width (spread).*—About 40.6 cm.

*Lateral branches.*—Length: About 19.8 cm. Diameter: About 2.2 mm. Internode length: About 3.6 cm. Aspect: Upright to decumbent. Texture: Pubescent. Color: Close to 144B.

Foliage description:

*Arrangement.*—Opposite, simple.

*Length.*—About 3.2 cm.

*Width.*—About 3 cm.

*Shape.*—Broadly ovate.

*Apex.*—Acute.

*Base.*—Cordate.

*Margin.*—Serrate.

*Texture, upper surface.*—Pubescent.

*Texture, lower surface.*—Smooth, glabrous.

*Venation pattern.*—Pinnate; reticulate.

*Color.*—Developing leaves, upper surface: Close to 143C. Developing leaves, lower surface: Close to 143D. Fully expanded leaves, upper surface: Close to N137C; venation, close to 144C. Fully expanded leaves, lower surface: Close to 138B; venation, close to 144C.

*Petiole.*—Length: About 1.1 cm. Diameter: About 1.3 mm. Texture, upper and lower surfaces: Smooth, glabrous. Color, upper and lower surfaces: Close to 144C.

Flower description:

*Flower type/habit.*—Single flowers borne in upper leaf axils; corolla bilabiate and calyx tubular; flowers face obliquely upright; freely flowering habit with about 175 flowers developing per plant.

*Fragrance.*—None detected.

*Natural flowering season.*—Plants begin flowering about three to four weeks after planting; long flowering period; continuously flowering from early summer to late autumn in Japan.

*Postproduction longevity.*—Flowers last about four days on the plant.

*Flower buds.*—Height: About 1.7 cm. Diameter: About 7.6 mm. Shape: Ellipsoidal. Color: Close to 144A; towards the apex, close to 187A.

*Flower diameter.*—About 3.2 cm by 3.3 cm.

*Flower depth.*—About 4.5 cm.

*Throat diameter.*—About 9.3 mm.

*Tube diameter, base.*—About 1.9 mm.

*Tube length.*—About 2.3 cm.

*Petals.*—Quantity per flower: Bilabiate with one upper or banner petal and one lower petal with two lateral and one lower lobes, petals fused. Upper petal: Length: About 1.4 cm. Width: About 2.3 cm. Shape: Elliptic. Apex: Mucronate to truncate. Margin: Entire; undulating. Texture, upper and lower surfaces: Smooth, glabrous. Color: Developing, upper and lower surfaces: Close to 9C faintly tinged with close to 83A. Fully developed, upper surface: Close to 8C to 8D faintly tinted with close to 83A. Fully developed, lower surface: Close to 9C faintly tinted with close to 83A. Lower petal: Length, lateral lobes: About 1.6 cm. Width, lateral lobes: About 1.1 cm. Length, lower lobe: About 1.4 cm. Width, lower lobe: About 2.2 cm. Shape, lateral and lower lobes: Elliptic. Apex, lateral lobes: Truncate. Apex, lower lobe: Rounded. Margin, lateral and lower lobes: Entire. Texture, lateral and lower lobes, upper and lower surfaces: Smooth, glabrous. Color, lateral lobes: Developing, upper surface: Close to 9A; towards the margins, close to 9A faintly tinted with close to 83A. Developing, lower surface: Close to 9B. Fully developed, upper surface: Close to 7B; towards the margins, close to 7B faintly tinted with close to 83A. Fully developed, lower surface: Close to 9B. Color, lower lobes: Developing, upper surface: Close to 9A; towards the margins, close to 9A faintly tinted with close to 83A; blotch, close to 12A. Developing, lower surface: Close to 9B. Fully developed, upper surface: Close to 9B; towards the margins, close to 9B faintly tinted with close to 83A; blotch, close to 12A. Fully developed, lower surface: Close to 9B. Throat color: Close to 83B. Tube color: Close to 83A.

*Sepals.*—Quantity per flower: Typically five, fused; ellipsoidal; margins winged. Calyx length: About 1.8 cm. Calyx diameter: About 8.4 mm. Texture, upper and lower surfaces: Smooth, glabrous. Color, immature, upper and lower surfaces: Close to 144A. Color, mature, upper surface: Close to 137C. Color, mature, lower surface: Close to 144A.

*Peduncles.*—Length: About 2.4 cm. Diameter: About 1.6 mm. Texture: Smooth, glabrous. Color: Close to 144B.

*Reproductive organs.*—Stamens: Quantity per flower: Typically four; two pairs of fused anthers. Filament length: About 4.6 mm to 12.8 mm. Anther shape: Ellipsoidal. Anther size: About 3 mm by 0.6 mm. Anther color: Close to 155C tinted with close to 79B. Pollen amount: Scarce. Pollen color: Close to 11B. Pistils: Quantity per flower: One. Pistil length: About 2.5 cm. Stigma shape: Elliptic. Stigma color: Close to N82D. Style color: Close to N81D. Ovary color: Close to 143C.

*Seed/fruit.*—Seed and fruit development have not been observed on plants of the new *Torenia*.

Disease/pest resistance: Plants of the new *Torenia* have not been noted to be resistant to pathogens and pests common to *Torenia*.

Garden performance: Plants of the new *Torenia* have been observed to have good garden performance and to tolerate rain, wind and temperatures from about 5° C. to about 30° C.

It is claimed:

1. A new and distinct *Torenia* plant named 'Sunrekodou' as illustrated and described.

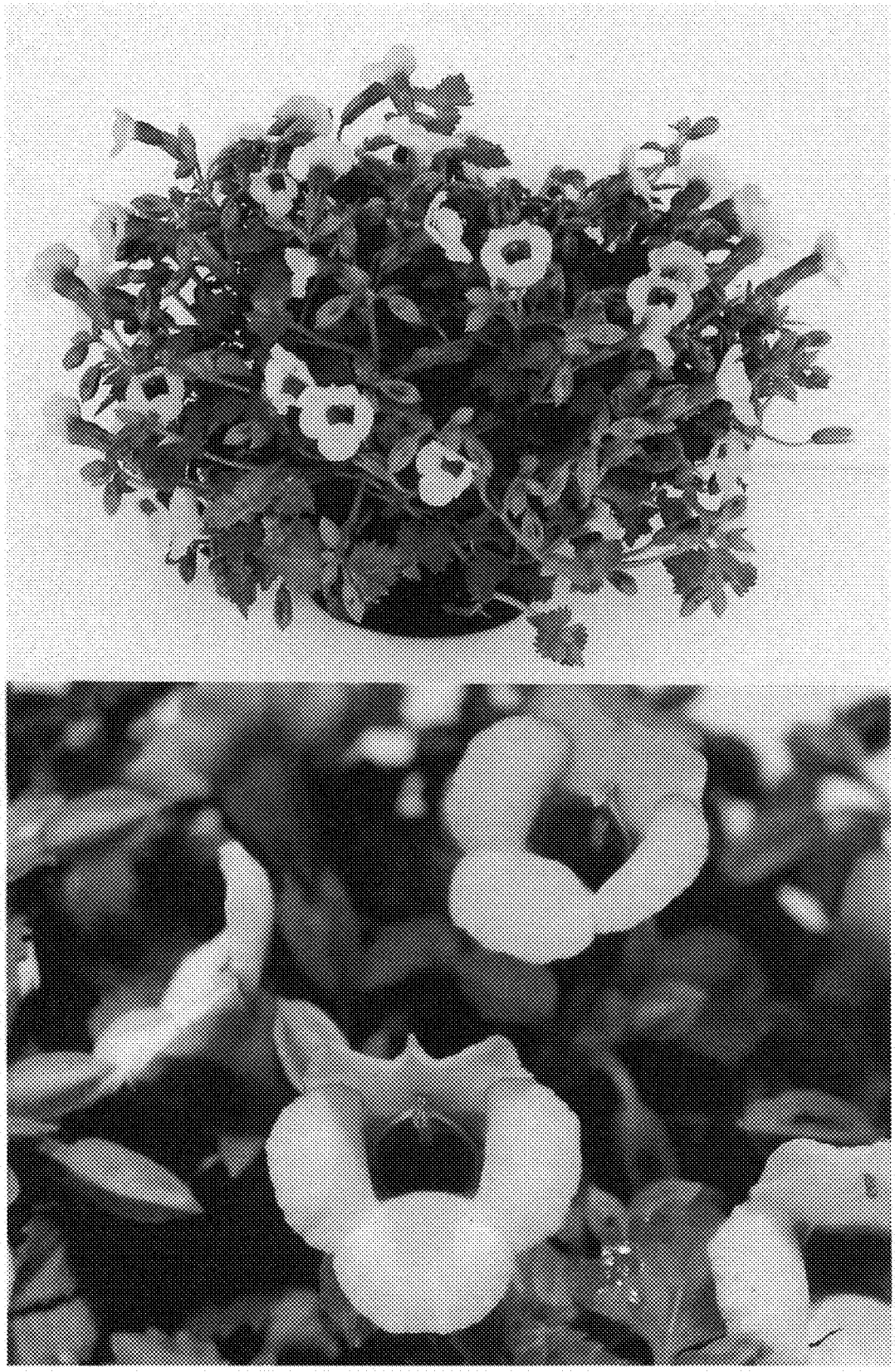

* * * * *